United States Patent
Schwantes et al.

(10) Patent No.: US 11,452,678 B2
(45) Date of Patent: Sep. 27, 2022

(54) ENCAPSULATION

(71) Applicant: Encapsys, LLC, Appleton, WI (US)

(72) Inventors: Todd Arlin Schwantes, Lena, WI (US); Diane Jean Williamson, Kaukauna, WI (US); Gregory Walter Perrine, Appleton, WI (US)

( * ) Notice: Subject to any disclaimer, the term of this patent is extended or adjusted under 35 U.S.C. 154(b) by 0 days.

(21) Appl. No.: 16/817,887

(22) Filed: Mar. 13, 2020

(65) Prior Publication Data
US 2020/0315931 A1   Oct. 8, 2020

Related U.S. Application Data

(60) Provisional application No. 62/818,852, filed on Mar. 15, 2019.

(51) Int. Cl.
| | |
|---|---|
| A61K 8/11 | (2006.01) |
| A61K 8/81 | (2006.01) |
| A61Q 13/00 | (2006.01) |
| A61Q 15/00 | (2006.01) |
| A61Q 19/00 | (2006.01) |
| C08F 220/06 | (2006.01) |
| A61Q 19/10 | (2006.01) |
| A61Q 5/02 | (2006.01) |

(52) U.S. Cl.
CPC .............. *A61K 8/11* (2013.01); *A61K 8/8147* (2013.01); *A61Q 5/02* (2013.01); *A61Q 13/00* (2013.01); *A61Q 15/00* (2013.01); *A61Q 19/10* (2013.01); *C08F 220/06* (2013.01)

(58) Field of Classification Search
CPC .......... A61K 8/11; A61K 8/8147; A61Q 5/02; A61Q 13/00; A61Q 15/00; C08F 220/06
See application file for complete search history.

(56) References Cited

U.S. PATENT DOCUMENTS

2011/0147961 A1*  6/2011  Schwantes
2011/0268778 A1*  11/2011  Dihora

\* cited by examiner

*Primary Examiner* — Alma Pipic
(74) *Attorney, Agent, or Firm* — Benjamin Mieliulis (57) ABSTRACT

The invention describes a core shell microcapsule wherein the capsule shell is hydrolysable. The capsule is made from a water phase with initiator and emulsifier, and from one or more oil phases having a first multifunctional (meth)acrylate monomer having greater than one ester group on average in the monomer and having a hydrophilicity index of less than 20; a second multifunctional (meth)acrylate monomer, the second multifunctional (meth)acrylate comprising a hydrophilic multifunctional polar monomer having a hydrophilicity index of at least 20 and said second multifunctional polar monomer comprising 50% or less of the capsule shell along with an acidic (meth)acrylate monomer or at least one oil soluble or dispersible simple acid, the acidic (meth)acrylate monomer having one or more groups which are selected from carboxy and sulfonic groups, and optionally from 0 to 50% by weight of the shell comprises in addition an aliphatic polyester comprising an oligomer, polymer or co-polymer of one or more of lactic acid, caprolactone, or glycolic acid, the aliphatic polyester having two or more of acrylate or methacrylate groups.

15 Claims, 3 Drawing Sheets

ENCAPSULATION

FIELD OF THE INVENTION

This invention relates to capsule manufacturing processes and microcapsules produced by such processes, along with improved articles of manufacture based on such microcapsules.

DESCRIPTION OF THE RELATED ART

Various processes for microencapsulation, and exemplary methods and materials are set forth in various patents, such as Schwantes (U.S. Pat. No. 6,592,990), Nagai et al. (U.S. Pat. No. 4,708,924), Baker et al. (U.S. Pat. No. 4,166,152), Woiciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Hayford (U.S. Pat. No. 4,444,699), Shioi et al. (U.S. Pat. No. 4,601,863), Kiritani et al. (U.S. Pat. No. 3,886,085), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103) and Greene et al. (U.S. Pat. Nos. 2,800,458; 2,800,457 and 2,730,456), among others and as taught by Herbig in the chapter entitled "Microencapsulation" in Kirk-Othmer Encyclopedia of Chemical Technology, V.16, pages 438-463.

Other useful methods for microcapsule manufacture are: Foris et al., U.S. Pat. Nos. 4,001,140 and 4,089,802 describing a reaction between urea and formaldehyde; Foris et al., U.S. Pat. No. 4,100,103 describing reaction between melamine and formaldehyde; and British Pat. No. 2,062,570 describing a process for producing microcapsules having walls produced by polymerization of melamine and formaldehyde in the presence of a styrene sulfonic acid. Alkyl acrylate-acrylic acid copolymer capsules are taught in Brown et al., U.S. Pat. No. 4,552,811. Each patent described throughout this application is incorporated herein by reference to the extent each provides guidance regarding microencapsulation processes and materials.

Interfacial polymerization is a process wherein a microcapsule wall or polyamide, an epoxy resin, a polyurethane, a polyurea or the like is formed at an interface between two phases. Riecke, U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in Greiner et al., U.S. Pat. No. 4,547,429. Matson, U.S. Pat. No. 3,516,941 teaches polymerization reactions in which the material to be encapsulated, or core material, is dissolved in an organic, hydrophobic oil phase which is dispersed in an aqueous phase. The aqueous phase has dissolved materials forming aminoplast (amine and aldehyde) resin which upon polymerization form the wall of the microcapsule. A dispersion of fine oil droplets is prepared using high shear agitation. Addition of an acid catalyst initiates the polycondensation forming the aminoplast resin within the aqueous phase, resulting in the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. Urea-formaldehyde (UF), urea-resorcinol-formaldehyde (URF), urea-melamine-formaldehyde (UMF), and melamine-formaldehyde (MF), capsule formations proceed in a like manner. In interfacial polymerization, the materials to form the capsule wall are in separate phases, one in an aqueous phase and the other in an oil phase. Polymerization occurs at the phase boundary. Thus, a polymeric capsule shell wall forms at the interface of the two phases thereby encapsulating the core material. Wall formation of polyester, polyamide, and polyurea capsules also typically proceed via interfacial polymerization.

Jahns, U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methyl methacrylate together with a free radical initiator.

Common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

Jabs et al., U.S. Pat. No. 4,947,152 teaches microcapsules with polyurea walls. The wall is the reaction product of an aromatic isocyanate with an isocyanate reactive group. The isocyanate reactive group can include di- and polyamines such as N-hydroxyethyl ethylenediamine, ethylene-1,2-diamine.

Hotz et al., U.S. Pat. Pub. 2013/0089590 teaches a fragrance microcapsule with a polyurea wall. The shell in the reaction product of at least two difunctional isocyanates and a difunctional amine.

EP 1693104 Maruyama discloses microcapsules having a polyurethane or polyurea wall obtained from polycondensation of a polyfunctional isocyanate with a polyfunctional alcohol or amine.

Schwantes, U.S. Pat. Pub. 2009/0274905 teaches cationic microcapsule particles where the wall is the reaction product of an amine acrylate with a multifunctional methacrylate in the presence of an acid and initiator; or alternatively an acid acrylate and multifunctional (meth)acrylate in the presence of a base and initiator.

A need exists in the art for capsules which have sufficient containment characteristics to effectively hold and protect the microcapsule core content yet which further fracture or degrade over time, preferably following use or upon release of the capsule contents. Such capsules reduce persistence in the environment and would be more acceptable for a variety of applications including application in sensitive environments.

The capsules of the invention exhibit excellent containment yet fracture and degrade over time following use. Surprisingly, the capsules of the invention incorporate acid hydrolysable groups, yet yield capsules stable in wet and acidic environments. This duality of character, stable yet degradable after use, is surprisingly achievable by incorporating a degradable group such as an acid hydrolysable group into a polyacrylate polymer from the oil side during encapsulation. In such manner, the degradable groups are protected until a time subsequent to use.

In the invention, The polymer shell of the capsules is modified by adding polar and hydrolysable groups to enable degradability to be realizable. The capsule shell, without modifications according to the invention, is hydrophobic. The surprising aspect of the invention is to modify the capsule polymer shell to increase its hydrophilicity. Modification of the capsule shell increases the number, type and/or concentration of polar hydrophilic groups and acid groups, and serves to position a portion of the additional hydrophilic and acid groups in the polymer to be accessible from the water side, the water-facing side of the capsule shell. This modification according to the invention is believed to enable a degree of inherent degradability of the capsule shell polymer to be not only enhanced but realized practically, such that the polymer which is typically hydrophobic and not readily attacked from the water side becomes more susceptible to degradation and/or hydrolysis. The polymer essentially has a latent aspect of degradability, which is more fully able to be realized, such as under composting conditions, by the modification of the invention. As a result, a polymer not normally hydrolysable in practice under normal conditions of use and disposal or at least not hydrolysable to the same extent, becomes able to be degraded particularly from attack, particularly on the water side. The added polar groups and acid groups make the polymer shell more vulnerable to water side attack. With increased hydrophilicity, the added groups help facilitate hydrolysis from the water side.

In the invention, a stable capsule with tight containment can be achieved, and yet further naturally fractured and degraded after use in the intended application. In one aspect the capsule comprises a layer, preferably an internal layer, of a polyacrylate having acid hydrolysable groups and optionally a thin outer shell of a second polymeric material without hydrolysable groups.

Definitions

As used herein, reference to the term "(meth)acrylate" or "(meth)acrylic" is to be understood as referring to both the acrylate and the methacrylate versions of the specified monomer, oligomer and/or prepolymer, (for example "multifunctional (meth)acrylate" indicates that both multifunctional methacrylate and multifunctional acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Each alkyl moiety herein, unless otherwise indicated, can be from $C_1$ to $C_8$, or even from $C_1$ to $C_{24}$. Poly(meth)acrylate materials are intended to encompass a broad spectrum of polymeric materials including, for example, polyester poly(meth)acrylates, urethane and polyurethane poly(meth)acrylates (especially those prepared by the reaction of an hydroxyalkyl (meth)acrylate with a polyisocyanate or a urethane polyisocyanate), methyl cyanoacrylate, ethyl cyanoacrylate, diethylene glycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetra ethylene glycol di(meth)acrylate, dipropylene glycol di(meth)acrylate, polyethylene glycol di(meth)acrylate, di(penta methylene glycol) di(meth)acrylate, ethylene di(meth)acrylate, neopentyl glycol di(meth)acrylate, trimethylolpropane tri(meth)acrylate, ethoxylated bisphenol A di(meth)acrylates, bisphenol A di(meth)acrylates, diglycerol di(meth)acrylate, tetra ethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates and multifunctional amine (meth)acrylates.

For purposes of the invention the term "degradable" is intended to be broadly construed and means that the shell wall, typically a copolymer, obtained by polymerizing one or more oil-soluble or oil-dispersible monomers, is capable of being depolymerized by hydrolysis such as in contact with low or high pH aqueous conditions, alternatively, degradation can be through action of intracellular or extra cellular depolymerases, photodegradation or disintegration through ultraviolet irradiation or heat exposure or chemical oxidation reducing the size of the polymer into smaller into smaller bits and fragments.

The term is intended to encompass depolymerization that occurs by mechanisms such as photodegradation and/or chemical degradation, hydrolysis or oxidation. The polymer shell of the capsules according to the invention is depolymerizable, in one aspect by having hydrolysable groups.

It is to be understood that depolymerization often can be less than 100% efficient, however, the occurrence of depolymerization of the shell copolymer can be measured by assessing the extent of reduction in mechanical properties over a set period of time in a standardized environment to mimic environmental aging effects.

Surprisingly, applicant is able to create a robust microcapsule utilizing monomers with ostensibly degradable moieties, however successfully achieving chemical encapsulation of core material forming shell at least in part or primarily from the oil phase. The moieties of the oil-soluble or oil-dispersible monomers add hydrophilic character to the monomers and resultant copolymer. The capsules are robust, yet hydrolysable and readily able to be depolymerized in the environment.

SUMMARY OF THE INVENTION

The invention comprises a microcapsule comprising a capsule core and a capsule shell, the capsule shell being hydrolysable. The microcapsule is made by an oil-in-water microencapsulation process comprising dispersing in an aqueous phase a polymeric emulsifier and optionally, an initiator; dispersing in one or more oil phases (i) an initiator, and a core material, (ii) a first multifunctional (meth)acrylate monomer having greater than one ester group on average in the monomer and having a hydrophilicity index of less than 20, (iii) a second multifunctional (meth)acrylate monomer, the second multifunctional (meth)acrylate comprising a hydrophilic multifunctional polar monomer having a hydrophilicity index of at least 20 and said second multifunctional polar monomer comprising 50% or less of the capsule shell, wherein the first and second multifunctional (meth)acrylate monomers together comprise greater than 80% by weight of the capsule shell, (iv) an acidic (meth)acrylate monomer or at least one oil soluble or dispersible simple acid or both, the acidic (meth)acrylate monomer having one or more groups which are selected from carboxy and sulfonic groups, and (v) optionally from 0 to 30% by weight or even from 0 to 50% by weight or even from 0.1 to 50% by weight of an aliphatic polyester, such as an aliphatic polyester comprising an oligomer, polymer or copolymer of lactic acid, glycolic acid, caprolactone, or combinations thereof, the aliphatic polyester capped by 2 or more acrylate or methacrylate groups; emulsifying the one or more oil phases into the water phase under high shear agitation to form an oil-in-water emulsion comprising droplets of the core material and oil phase monomers dispersed in the water phase; and activating the initiator or initiators by heat or actinic radiation to react the monomers forming a polymeric shell surrounding the droplets of the emulsion. The microcapsules when measured under controlled composting conditions at 6 months from making, have a percent reduction of the microcapsules of at least 15% by weight.

In certain embodiments, the multifunctional (meth)acrylate monomer having greater than one ester group on average in the monomer has an average number of ester groups of at least 1.5.

In a further embodiment, the first multifunctional (meth) acrylate monomer having greater than one ester group on average in the monomer is selected from the group of multifunctional (meth)acrylate monomers consisting of ethylene glycol dimethacrylate, trimethylolpropane triacrylate, trimethylolpropane trimethacrylate, pentaerythritol tetraacrylate, tricyclodecane dimethanol dimethacrylate, 1,10 decanediol dimethacrylate, 1,6 hexanediol dimethacrylate, 1,9 nonanediol dimethacrylate, neopentyl glycol dimethacrylate, di-trimethylolpropane tetraacrylate, dipentaerythritol pentaacrylate, ethoxylated (2) bisphenol A dimethacrylate, 2,2 bis[4-(methacyloyl ethoxy) phenyl] propane, ethoxylated (3) bisphenol A diacrylate, dipropylene glycol diacrylate, ethoxylated (4) bisphenol A diacrylate, ethoxylated (4) bisphenol A dimethacrylate, 2,2 bis[4-(methacyloyl ethoxy) phenyl] propane and pentaerythritol triacrylate.

In a yet further embodiment of the microcapsule inventions, the hydrophilic multifunctional polar monomer is selected from polyethylene glycol 200 dimethacrylate, ethoxylated (9) trimethylolpropane triacrylate, 2,2 bis[4-(methacyloyl ethoxy) phenyl] propane, ethoxylated (30) BPA diacrylate, ethoxylated (15) trimethylolpropane triacrylate, ethoxylated glycerine triacrylate, ethoxylated (20) trimethylolpropane triacrylate, polyethylene glycol 400 dimethacrylate, polyethylene glycol 600 dimethacrylate, ethoxylated glycerine triacrylate, ethoxylated pentaerythritol tetraacrylate, polyethylene glycol 1000 dimethacrylate, polyethylene (200) glycol dimethacrylate, polyethylene glycol (200) diacrylate, polyethylene glycol (400) diacrylate, polyethylene glycol (600) diacrylate and tris (2-hydroxy ethyl) isocyanurate triacrylate.

In an alternative embodiment the second multifunctional methacrylate monomer has a hydrophilicity index of at least 30 and said second multifunctional methacrylate monomer is selected from the group consisting of diethylene glycol dimethacrylate, ethoxylated (3) trimethylolpropane triacrylate, polypropylene glycol 400 dimethacrylate, ethoxylated (10) bisphenol A dimethacrylate, ethoxylated (10) bisphenol A diacrylate, 2,2 bis[4-(methacyloyl ethoxy) phenyl] propane, ethoxylated (4) pentaerythritol tetraacrylate, triethylene glycol dimethacrylate, 2-hydroxyl 1-3 dimethacryloxy propane, ethoxylated (6) trimethylolpropane triacrylate, ethoxylated propyleneglycol dimethacrylate and 2,2 bis[4-(methacyloyl ethoxy) phenyl] propane.

DETAILED DESCRIPTION

The microcapsules according to the invention comprise a core shell structure. In the absence of modification, capsules based on multifunctional (meth)acrylates generally are not hydrolysable as the shell is hydrophobic.

In the invention, the polymer shell of the capsules is modified to add polar and optionally additional hydrolysable groups to make the inherent degradability realized by facilitating hydrolysis from the water side of the capsule shell. The capsule shell, without modifications according to the invention, is hydrophobic. The surprising aspect of the invention is that modification of the shell with hydrophilic groups allows the inherent degradability of existing functionality to be realized in the formulation. The added polar groups and acid groups make the polymer shell more vulnerable to water side attack. With increased hydrophilicity, the added groups help facilitate hydrolysis from the water side. Surprisingly the capsule shell is hydrolysable yet able to form a durable benefit agent delivery particle or microcapsule.

In microencapsulation, a core material of liquid or solid benefit agent is surrounded with a polymeric shell or alternatively embedded in a matrix of the polymer shell or a secondary polymer or gel.

Release is achieved through fracture, diffusion or other chemical or physical factors. In some embodiments, retention over a prolonged time period is desirable. In alternative embodiments release and further degradation through hydrolysis is desirable to facilitate reduction in mechanical properties and degradation with environmental aging.

The microcapsules of the invention are made by a process involving creating an aqueous phase with a polymeric emulsifier and an initiator. One or more oil phases have dispersed therein one or more multifunctional (meth)acrylate monomers with ester groups and an acidic (meth) acrylate monomer or at least one oil soluble or dispersible simple acid.

High shear agitation is used to emulsify the one or more oil phases into the water phase. The free radical initiators of the water phase are activated by heat of actinic radiation, forming a polymeric film constituting the polymer shell surrounding emulsified droplets or particles of the core.

The oil phases of the process of the invention are emulsified into the water phase, forming an oil in water emulsion. The monomers of the oil phase react when in proximity in a chain growth polymerization reaction promoted by initiators in the immiscible water phase. The oil is emulsified to a desired droplet size of oil dispersed in the water phase. The solubility and partition coefficient of the monomers tends to control the localization of the reaction site at the interface of the oil in water droplets.

After a desired droplet size is attained and emulsion is stabilized with polymeric emulsifier, the chain growth reaction of the monomers results in a membrane forming on the droplets at the interface. The resultant microcapsules are of a particle size of 0.1 to 150 microns, 0.5 to 100 microns or even from 1 to 100 microns.

In certain embodiments where the monomers are more soluble in the oil phase or phases it is possible to form a matrix capsule, though in the process of the invention, a core-shell microcapsule is preferred.

The microcapsules of the invention while robust, yet exhibit depolymerization in the environment. This surprising attribute is achieved by selecting multifunctional (meth)acrylate monomer having greater than one ester group on average in the monomer, incorporating hydrophilic monomers, optionally additional hydrolysable functionality, and optionally acid monomers to the polymer structure, in order to facilitate the hydrolysis of the inherently hydrolysable groups that are otherwise inhibited from such hydrolysis.

The polymer shell of the microcapsule, when formed of the reaction product of monomers with greater than one ester group, is hydrolysable, desirably fostering depolymerization of the capsule shell in the environment.

The first multifunctional (meth)acrylate monomer of the invention has greater than one ester group on average in the monomer, and in the invention is the primary hydrolysable monomer forming the capsule shell when polymerized.

The microcapsules, when measured under controlled composting conditions for 6 months from making, typically have a percent reduction of the microcapsules of at least 15% by weight. When measured under controlled conditions in a hemocytometer counting chamber, the microcapsules have an average rate of observed loss of at least 1% per day.

The primary hydrolysable monomer has greater than one ester group on average in the monomer. Monomers with more than one ester group desirably predominate, such that the ester groups average more than one ester group. The ester groups remain available as hydrolysable sites of the shell polymer. The multifunctional (meth)acrylate monomer has greater than one ester group on average in the monomer and has an average number of ester groups of at least 1.5.

A secondary hydrolysable monomer or bio reducible monomer, optionally and in addition, can be used in formation of the capsule shell and can comprise the capsule shell at from 0 to 30%, or even 0 to 50% or even 0.1 to 50% by weight of the capsule shell, selected from monomers having lactic acid, glycolic acid, disulfide, imine, acetal, ketal, hemiacetal, hemiketal, aminal, hemiaminal, thioacetal, thioketal, orthoformate, lactic-acid-co-glycolic acid, caprolactone, phosphoester, phosphase, anhydride, orthoester, polyester or formate content. To incorporate these monomers into the capsule shell, these monomers are typically fashioned into and used as oligomers or polymers as aliphatic polyesters having two or more acrylate or methacrylate groups.

Polyester (meth)acrylates include, for example, acrylate resins available as polyester oligomers such as Sartomer CN 2203™, 2207™ and 2262™ polyester acrylates and the like.

In the invention, typically from 1% to 100% particles are of a particle size of from 0.1 to 150 microns, or even 0.5 to 100 microns, or even from 1 to 100 microns. Each particle comprises a core that comprises, based on total weight, from about 2% to about 99.9% of a benefit agent and, optionally in some embodiments, from 0.1% to about 98% of a partitioning modifier, wherein the benefit agent and the partitioning modifier are different materials. The shell, using a secondary hydrolysable monomer can optionally comprise up to 50% of at least one monomer selected from a monomer having at least one of disulfide, acetal, hemiacetal, ketal, hemiketal, aminal, hemiaminal, thioacetal, thioketal, orthoformate, lactic acid, glycolic acid, lactic-acid-co-glycolic acid, caprolactone, phosphoester, phosphase, anhydride, orthoester or formate content together with the multifunctional (meth)acrylate monomer comprising a polar multifunctional (meth)acrylate and the multifunctional (meth)acrylate having greater than one ester group on average in the monomer. The shell can comprise, based on total shell weight, from about 30% to about 100% of the poly(meth)acrylate. When the monomers are reacted to form the shell, the polymer forms a poly(meth)acrylate random copolymer. In a further embodiment, the shell capsule can comprise a reaction product of an additional monomer selected from a disulfide, an acetal, a hemiaminal, a thioacetal, a thioketal, a formate, a phosphoester, a phosphase, an anhydride or an orthoester monomer, said additional monomer based on total shell weight constituting from 0.1 to 50% of the capsule shell.

The shell wall of the microcapsules comprises a poly (meth)acrylate functionalized or random copolymer derived from the oil phase obtained by polymerizing the one or more oil soluble or dispersible monomers having at least one hydrolysable moiety.

In certain embodiments, the hydrolysable moiety can be selected from, based on total shell weight: (a) from about 0.2 to 11 wt % acetal or hemiacetal content; (b) from about 0.2 to 18 wt % lactic acid, glycolic acid or lactic-co-glycolic acid content; (c) from 0.2 to 18 wt % caprolactone content; or (d) from 0.1 to 22 wt % phosphoester, polyester or phosphase content, but are not limited to such. Content refers to the weight of the specific identified groups.

The multifunctional (meth)acrylates, for example, can be blended and co-reacted with polylactic acid diacrylate or dimethacrylate, polyglycolic acid diacrylate or dimethacrylate, polycaprolactone diacrylate or dimethacrylate, a diacrylate or a di(meth)acrylate monomer containing disulfide linkages or acetal or hemiacetal functional groups. Useful monomers for copolymerization include polylactic acid dimethacrylate, polylactic acid diacrylate, polyglycolic acid dimethacrylate, polyglycolic acid diacrylate, polycaprolactone dimethacrylate, polycaprolactone dimethacrylate, disulfide dimethacrylate, disulfide diacrylate, or bis (2-methacryloyl) oxyethyl disulfide.

The microcapsules can be used dry or as a slurry of microcapsules, in coatings, as an additive to other materials, incorporated in or on fibers or textiles, or incorporated in or on polymeric materials, foams or other substrates. Optionally after microcapsule formation, the formed microcapsule can be isolated from the water phase or continuous phase, such as by decanting, dewatering, centrifuging, spray-drying, evaporation, freeze drying or other solvent removal or drying process.

The capsules according to the invention are useful with a wide variety of capsule contents ("core materials" or "benefit agents") including, by way of illustration and without limitation, internal phase oils, solvent oils, phase change materials, lubricants, dyes, perfumes, fragrances, cleaning oils, polishing oils, flavorants, nutrients, sweeteners, chromogens, pharmaceuticals, fertilizers, herbicides, biological actives, scents, and the like. The microcapsule core materials can include materials which alter rheology or flow characteristics or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material typically should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

Useful benefit agents or core materials include perfume raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, biological actives, deodorants, emollients, humectants, exfoliants, ultraviolet absorbing agents, self-healing compositions, corrosion inhibitors, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as core materials can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase change materials can alternatively, optionally in addition include crystalline materials such as 2,2-dimethyl-1,3-propanediol, 2-hydroxymethyl-2-methyl-1, 3-propanediol, acids of straight or branched chain hydrocarbons such as eicosanoic acid and esters such as methyl palmitate, fatty alcohols and mixtures thereof. Blends of capsule populations can be useful, such as with differing sets of benefit agent, or even different wall formulations A partitioning modifier can optionally also be included as a constituent of the microcapsule core. The partitioning modifier can be the same material as the oil phase or diluent or can be different. The partitioning modifier can be selected from a larger group and can be further selected from the group consisting of oil soluble materials that have a C log P greater than from about 4, or from about 5, or from about 7, or even from about 11 and/or materials that also have a density higher than 1 gram per cubic centimeter.

The invention makes possible both hydrolysable groups incorporated into the shell and tailored positive or negative surface charge of (meth)acrylate-based microcapsules by chemical attachment to the shell, through the charged domains or charged pendant groups of the resulting polymer. Cationic microcapsules are useful to improve deposition and adherence to substrates.

Surface charge can be added with deposition aids or charged groups to improve the deposition of the microcapsules on substrates such as textiles, skin, hair, fibers, or other surfaces. In certain embodiments the resultant microcapsules are cationic. Surface charge can also be advantageously employed to improve adhesion of microcapsules on surfaces such as foam or bedding material.

Deposition aids can include poly (acrylamide-co-diallyldimethylammonium chloride, poly (diallyldimethylammonium chloride, polyethylenimine, cationic polyamine, poly [(3-methyl-1-vinylimidazolium chloride)-co-(1-vinylpyrrolidone)], copolymer of acrylic acid and diallyldimethylammonium chloride, cationic guar, guar gum, an organopolysiloxane such as described in US Publication 20150030557, incorporated herein by reference. In a further embodiment, the above-described microcapsules can comprise a deposition aid, and in a further aspect the deposition aid coats the outer surface of the shell of the microcapsule. Deposition aids can be coated onto capsules or covalently bonded, employing functional groups to effect linkage as generally described in Universidade do Minho, WO 2006117702; Gross et al., US 20170296440; and Devan Micropolis, US 20080193761

In a further aspect the deposition aid can comprise a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a yet further aspect, the deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methacrylate, polyvinylpyrrolidone-vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

Surface charge can also be advantageously adapted to create agglomerates to facilitate ease of filtration where a high solids, cake, or dry powder of microcapsules is desirable.

If desired the microcapsules can be separated from the aqueous medium. The slurry can either be used as is, used as a dewatered cake, or used in dry powder form depending on the application.

A multifunctional monomer for the oil phase is selected based on its hydrophilicity index (HPI). Hydrophilicity index is defined as the weight percentage of oxygen and nitrogen in the non-acrylate or non-methacrylate portion of the monomer molecule.

$$HPI = \frac{\text{weight of oxygen} + \text{weight of nitrogen}}{\text{total weight of monomer}} \times 100$$

In the calculation, the oxygen and nitrogen in the acrylate moiety or methacrylate moiety is included in the denominator but omitted from the numerator. The HPI index correlates to a relative increase or decrease in water or oil solubility contributed by parts of the molecule other than the acrylate or methacrylate moiety.

Table 1 provides an illustrative list of the hydrophilicity index of various monomers.

TABLE 1

| Material | Name | HPI |
| --- | --- | --- |
| 701 | 2-hydroxyl 1-3 dimethacryloxy propane | 27.59 |
| 1206PE | ethoxylated propyleneglycol dimethacrylate (PO12/EO6) | 28.81 |
| 14G | polyethylene glycol 600 dimethacrylate | 34.67 |
| 23G | polyethylene glycol 1000 dimethacrylate | 35.34 |
| 2G | diethylene glycol dimethacrylate | 22.22 |
| 3G | triethylene glycol dimethacrylate | 27.59 |
| 4G | polyethylene glycol 200 dimethacrylate | 30.00 |
| 9G | polyethylene glycol 400 dimethacrylate | 33.68 |
| 9PG | polypropylene glycol 400 dimethacrylate | 24.62 |
| A-GLY-20E | ethoxylated glycerine triacrylate (EO 20 mol) | 34.74 |
| A-GLY-9E | ethoxylated glycerine triacrylate (EO 9 mol) | 32.95 |
| ATM-35E | ethoxylated pentaerythritol tetraacrylate (EO 35 mol) | 34.83 |
| BPE-100 | 2,2 bis[4-(methacyloyl ethoxy) phenyl] propane (EO 2.6 mol) | 13.49 |
| BPE-1300N | 2,2 bis[4-(methacyloyl ethoxy) phenyl] propane (EO 30 mol) | 31.70 |
| BPE-200 | 2,2 bis[4-(methacyloyl ethoxy) phenyl] propane (EO 4 mol) | 17.30 |
| BPE-500 | 2,2 bis[4-(methacyloyl ethoxy) phenyl] propane (EO 10 mol) | 25.24 |
| BPE-80N | 2,2 bis[4-(methacyloyl ethoxy) phenyl] propane (EO 2.3 mol) | 12.47 |
| BPE-900 | 2,2 bis[4-(methacyloyl ethoxy) phenyl] propane (EO 17 mol) | 28.87 |
| DCP | tricyclodecane dimethanol dimethacrylate | 0.00 |
| DOD-N | 1,10 decanediol dimethacrylate | 0.00 |
| HD-N | 1,6 hexanediol dimethacrylate | 0.00 |
| NOD-N | 1,9 nonanediol dimethacrylate | 0.00 |
| NPG | neopentyl glycol dimethacrylate | 0.00 |
| SR206 | ethylene glycol dimethacrylate | 0.00 |
| SR210 | polyethylene (200) glycol dimethacrylate | 36.36 |
| SR259 | polyethylene glycol (200) diacrylate | 36.36 |
| SR295 | pentaerythritol tetraacrylate | 0.00 |
| SR344 | polyethylene glycol (400) diacrylate | 36.36 |
| SR348 | ethoxylated (2) bisphenol A dimethacrylate | 11.35 |
| SR349 | ethoxylated (3) bisphenol A diacrylate | 14.72 |
| SR350 | trimethylolpropane trimethacrylate | 0.00 |
| SR351 | trimethylolpropane triacrylate | 0.00 |
| SR355 | di-trimethylolpropane tetraacrylate | 8.79 |
| SR368 | TRIS (2-HYDROXY ETHYL) ISOCYANURATE TRIACRYLATE | 42.86 |
| SR399 | dipentaerythritol pentaacrylate | 10.53 |
| SR415 | ethoxylated (20) trimethylolpropane triacrylate | 33.23 |
| SR444 | pentaerythritol triacrylate | 18.82 |
| SR454 | ethoxylated (3) trimethylolpropane triacrylate | 22.33 |
| SR480 | ethoxylated (10) bisphenol A dimethacrylate | 25.24 |
| SR494 | ethoxylated (4) pentaerythritol tetraacrylate | 26.23 |
| SR499 | ethoxylated (6) trimethylolpropane triacrylate | 27.67 |
| SR502 | ethoxylated (9) trimethylolpropane triacrylate | 30.06 |
| SR508 | dipropylene glycol diacrylate | 16.00 |
| SR540 | ethoxylated (4) bisphenol A dimethacrylate | 17.30 |
| SR601 | ethoxylated (4) bisphenol A diacrylate | 17.30 |
| SR602 | ethoxylated (10) bisphenol A diacrylate | 25.24 |
| SR610 | polyethylene glycol (600) diacrylate | 36.36 |
| SR9035 | ethoxylated (15) trimethylolpropane triacrylate | 32.30 |
| SR9038 | ethoxylated (30) BPA diacrylate | 31.70 |
| | ethylidene dimethacrylate | 0.00 |

Capsule Degradation Test

Hydrolysis of the capsule materials was assessed by simulating controlled composting conditions of oxygen, moisture, temperature and pH. Such conditions, for example, can be usefully adapted from ISO 14855.

Figure 1:
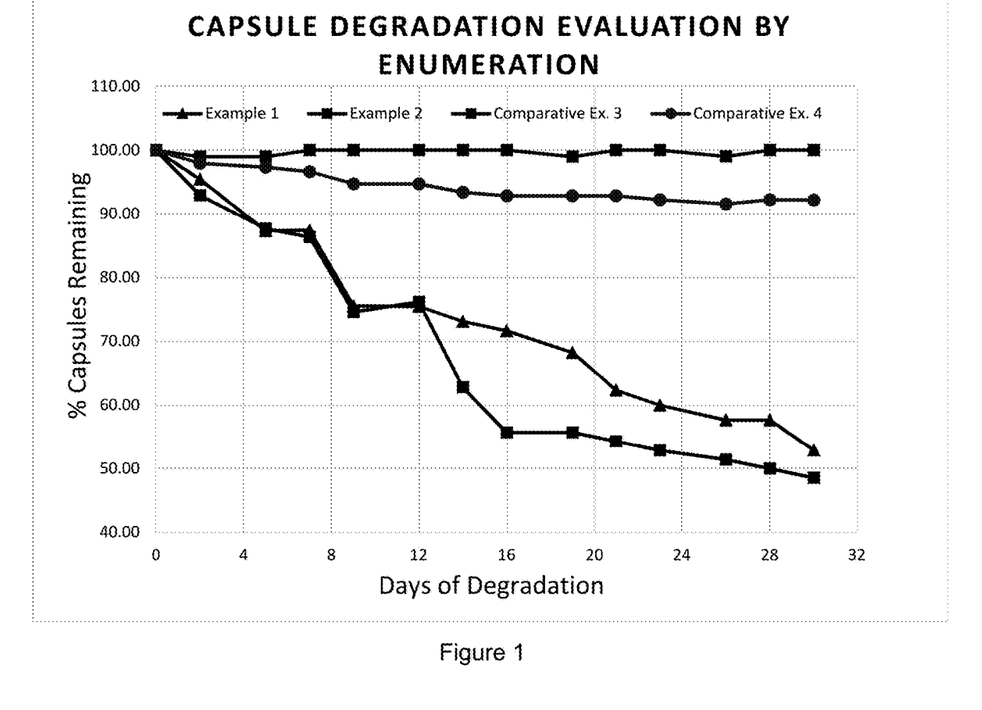
FIG. 1 depicts results of capsule degradation ascertained by an enumeration method, using a hemocytometer counting chamber.

In FIG. 1 comparison is made of capsules according to the invention and capsules without the extra ester groups, acid methacrylate and polar multifunctional (meth)acrylate of the invention. The percentage of capsules remaining is measured over a span of time. Capsules according to the invention display more rapid loss of weight as compared to the controls, and lose more mass than the comparatives over the same time period.

Enumeration Analysis

Enumeration using phase-contrast microscopy is accomplished with a Hemacytometer Counting Chamber (Hauser-Scientific 3900) device. Each sample is combined with activated sludge from a local wastewater treatment plant at a 1:500 dilution. The sample was held in a water bath at 38.1° C. for 30 days and stirred every 6 hours using an Automatic Methane Potential Test System (AMPTS). Results are depicted in FIG. 1. Degradation can be measured as the observed loss in number of observable capsules in a fixed period of time, such as 30 days or six months or other fixed period. FIG. 1 presents degradation data after 30 days. In FIG. 1, after 30 days for Examples 1 and 2, the degradation rate exceeds more than 1% per day on average, more particularly the rate being 1.6% per day for Example 1 and 1.7% for Example 2.

Based on the counting device results averaged over 30 days, capsule degradation in activated sludge of a wastewater treatment plant was measured. As can be seen in FIG. 1, Example 1 capsules degraded at an average rate of 1.6% per day. Example 2 capsules degraded at an average rate of 1.7% per day. Comparative Example 3 capsules degraded at a rate of 0% per day. Comparative Example 4 capsules degraded at a rate of 0.26% per day.

FIG. 1 graphs the percent of microcapsules remaining based on measurements by enumeration of microcapsules of Examples 1 and 2, and Comparative Examples 3 and 4.

Figure 2:
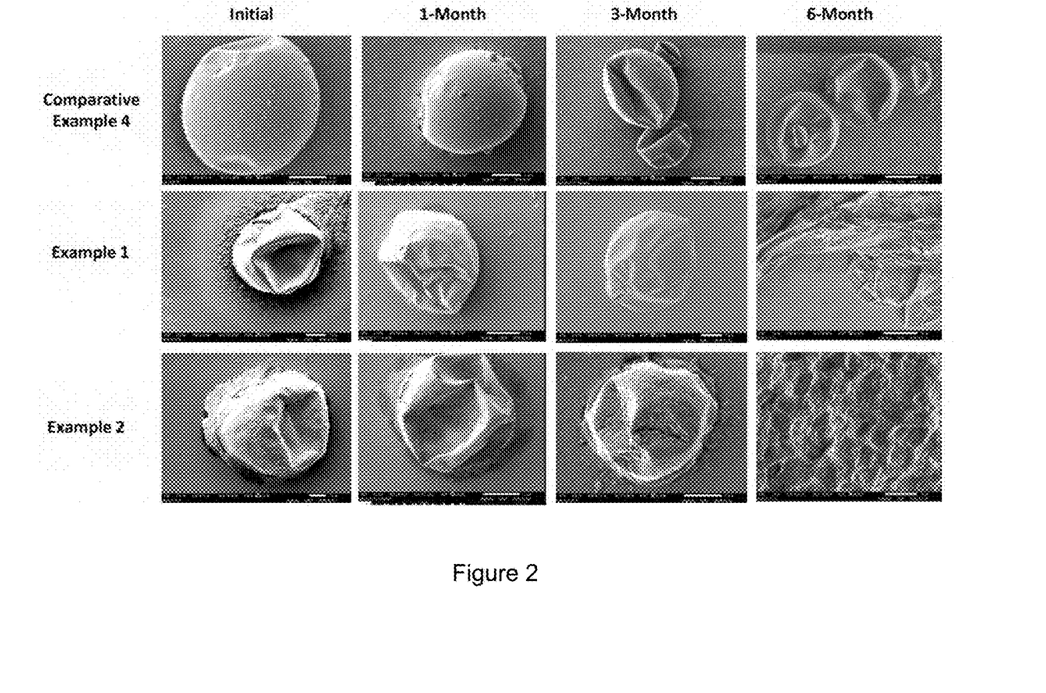
FIG. 2 are photomicrographs illustrating results of degradation by hydrolysis, wherein results of several microcapsules over set periods of time are visually presented.

In FIG. 2, the degradation results of other samples of several microcapsules according to the examples, over set periods of time, are visually presented. FIG. 2 presents photomicrographs showing visually observable results. For these samples of capsules according to the examples, the capsule slurry was diluted to 10% solids and subjected to constant agitation. At t=0, 1, 3 and 6 months, a sample was removed and dried on a slide. The slide was sputter-coated, and images were taken on a scanning electron microscope at varying magnifications between 300× and up to 7500×. In FIG. 2, for capsules according to Examples 1 and 2, it can be seen that capsules are no longer observed. Contrast the photo of Comparative Example 4 clearly depicting observable capsules.

The microcapsules of the invention can be incorporated dry, as an aqueous slurry, as a coating or as a gel into a variety of commercial products to yield novel and improved articles of manufacture, including incorporation into or onto foams, mattresses, bedding, cushions, added to cosmetics or to medical devices, incorporated into or onto packaging, dry wall, construction materials, heat sinks for electronics, cooling fluids, incorporated into insulation, used with lotions, incorporated into gels including gels for coating fabrics, automotive interiors, and other structures or articles, including clothing, footwear, personal protective equipment and any other article where use of the improved capsules of the invention is deemed desirable. The articles of manufacture can be selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a foam, a pillow, a mattress, bedding, a cushion, a cosmetic, a medical device, an agricultural product, packaging, a cooling fluid, a wallboard, and insulation.

The microcapsules protect and separate the core material such as phase change material or fragrance or other core material or benefit agent, keeping it separated from the external environment. This facilitates design of distinct and improved articles of manufacture. The microcapsules facilitate improving flowability of encapsulated materials enhancing ease of incorporation into or onto articles such as foams, gels, textiles, various cleaners, detergents or fabric softeners. The microcapsules can be used neat, or more often blended into coatings, gels or used as an aqueous slurry or blended into other articles to form new and improved articles of manufacture. For example, with phase change benefit agents, the microcapsules help preserve the repeated activity of the phase change material and retain the phase change material to prevent leakage or infusion into nearby components when isolation of the microcapsules is desired, yet promote eventual degradation of such encapsulates or portions of the articles of manufacture.

Examples

In the following examples, the abbreviations correspond to the following materials:

TABLE 1

| | Company/City | |
|---|---|---|
| V50 | Wako Specialty Chemicals, Richmond, VA | 2,2'-azobis (2-methylpropionamidine) dihydrochloride |
| SR415 | Sartomer Company, Exton, PA | ethoxylated trimethylolpropane triacrylate |
| CD9055 | Sartomer Company, Exton, PA | carboxylic acid monofunctional acrylate monomer |
| SR206 | Sartomer Company, Exton, PA | ethylene glycol dimethacrylate |
| Vazo 67 | Chemours Company, Wilmington, DE | 2,2'-azobis (2-methylbutyronitrile) |
| Vazo 88 | Chemours Company, Wilmington, DE | 1,1'-azobis cyclohexane carbonitrile |
| TBAEMA | Sigma Aldrich, St. Louis, MO | 2-(tert-butylamino) ethyl methacrylate |
| Captex 355 | Abitec, Columbus, OH | caprylic/capric triglyceride |
| PLA-DM | | poly lactic acid dimethacrylate |

The process description for each of the following examples is as follows. An oil phase one is prepared in a 1-liter jacketed reactor with milling, while adding fragrance oil/diluent oil and initiators. The oil phase is equilibrated and held at 60° C. for at least 20 minutes for pre-reaction. An oil phase two is prepared in a separate reactor with stirring and is comprised of additional fragrance oil, wall material and polar monomers. Prior to the end of the first pre-reaction, oil phase two is pre-heated using a 60° C. water bath. After the oil phase one pre-reaction, the pre-heated oil phase two is added and held for 30 minutes. A water phase, consisting of water, PVOH and a water phase initiator is prepared in a large beaker with stirring. The water phase is pre-heated to 60° C. for 30 minutes. Agitation of the combined oil phases is stopped, and water phase is added and milled for 60 minutes. The milling temperature is set at 60° C. for the first 30 minutes and then raised to 75° C. with further mixing. Temperature is raised further to 95° C. over 7 hours and held for 6 hours.

Example 1

Oil phase one is prepared with 62.72 g of perfume oil and 67.68 g of a diluent oil, along with 0.29 g each of two initiators, Vazo 67 and Vazo 88. Oil phase two is prepared with 20 g of perfume oil, 7.35 g of SR415, 6.3 g of SR206, 6.3 g of poly(D,L-lactide) dimethacrylate and 1.05 g of CD9055. The water phase is comprised of 45.0 g of a 5% polyvinyl alcohol solution, 235.0 g of water and 0.3 g of V-50 water phase initiator.

Example 2

Oil phase one is prepared with 62.72 g of perfume oil and 67.68 g of a diluent oil, along with 0.29 g each of two initiators, Vazo 67 and Vazo 88. Oil phase two is prepared with 20 g of perfume oil, 7.35 g of SR415, 6.3 g of SR206 and 6.3 g of poly(D,L-lactide) dimethacrylate. In addition, 1.05 g of 2-sulfoethyl methacrylate is added at the same time as oil phase two, but is added directly to the reactor and not pre-heated. The water phase is comprised of 45.0 g of a 5% polyvinyl alcohol solution, 235.0 g of water and 0.3 g of V-50 water phase initiator.

Example 3

Oil phase one is prepared with 62.72 g of perfume oil and 67.68 g of a diluent oil, along with 0.29 g each of two initiators, Vazo 67 and Vazo 88. Oil phase two is prepared with 20 g of perfume oil, 20.4 g of SR206, 0.3 g of CD9055 and 0.3 g TBAEMA. The water phase is comprised of 45.0 g of a 5% polyvinyl alcohol solution, 235.0 g of water and 0.3 g of V-50 water phase initiator.

Example 4

Oil phase one is prepared with 62.72 g of perfume oil and 67.68 g of a diluent oil, along with 0.29 g each of two initiators, Vazo 67 and Vazo 88. Oil phase two is prepared with 20 g of perfume oil, 15.3 g of SR206, 6.3 g of poly(D,L-lactide) dimethacrylate, 0.3 g of CD9055 and 0.3 g TBAEMA. The water phase is comprised of 45.0 g of a 5% polyvinyl alcohol solution, 235.0 g of water and 0.3 g of V-50 water phase initiator.

Example 5

Capsules were prepared using ethylidene dimethacrylate material. Acetal-functionalized monomers are typically acid-degradable at pH values even weakly acidic, such as pH of 5.5. A description of the batch follows:

Oil Phase 1:
135.4 g Captex 355
0.071 g Vazo-67
0.071 g Vazo-88

Oil Phase 2:
15 g Captex 355
5 g ethylidene dimethacrylate (acetal dimethacrylate)
0.08 g CD9055
0.08 g TBAEMA Water Phase:
45 g 5% 540 PVOH
235 g water
0.073 g V50

Oil 1 was added under a nitrogen blanket to a 40° C. reactor with mixing at 750 rpm (4-tip flat mill) and a nitrogen blanket. It was heated from 40° C. to 60° C. over 45 minutes and held at 60° C. for 2 hours. Oil phase 2 (which was pre-heated to 60° C.) was added and the combined oils were mixed for 10 minutes. Mixing was stopped, the pre-heated water phase (60° C.) was added and mixing was started again at 2500 rpm. Milling continued for 30 minutes at 60° C. and then the batch temperature was increased to 75° C. over the next 30 minutes of milling. After 60 minutes of total milling, batch mixing was continued at 350 rpm. The batch was heated from 75° C. to 95° C. over 7 hours and held at 95° C. for 6 hours. Final capsule size was about 19 microns. Leakage data for two samples of this batch is listed in Table 2.

TABLE 2

| Sample | Free-oil (avg) | Total oil (% of actives) | Hexane leakage-1 day | Hexane leakage-1 week | Hexane leakage-2 weeks | Hexane leakage-4 weeks |
|---|---|---|---|---|---|---|
| A | 0.0539 | 0.112% | 0.53 | 1.41 | 2.01 | 2.32 |
| B | 0.0114 | 0.025% | 0.69 | 1.09 | 1.34 | 1.70 |

These two samples were exposed to low pH conditions of 2.20 and 4.5 with the expectation that the capsules would easily degrade and release all core contents. The capsules did not degrade at low pH, even after 2 or more days of exposure of the capsules to the acid conditions, which was unexpected given the acid-degradability of the wall material. Results are shown in Table 3 below.

TABLE 3

| Sample | pH | Free-oil (%) Day 1 | Free-oil (%) Day 2 |
|---|---|---|---|
| A |  | 0.0411 | — |
| A | 2.20 | not detected | 0.0495 |
| A | 4.50 | 0.0111 | 0.0503 |
| B |  | not detected | — |
| B | 2.20 | not detected | 0.0267 |
| B | 4.50 | not detected | 0.0505 |

Examples 6-10

The following example 6 uses acetal monomer as the primary wall material. The additional examples use acetal monomer or ethylene glycol dimethacrylate as the primary wall material, with polyethylene glycol diacrylate replacing some of the primary wall material. The capsule core consists of a 50/50 mix of capric/caprylic acid triglyceride and ethyl heptanoate. The composition for example 6 is shown in Table 4.

TABLE 4

| Example 6 Composition | Amount (g) |
|---|---|
| Oil Phase 1 | |
| 50/50 Captex 355/ethyl heptanoate | 135.4 |
| Vazo-67 | 0.2 |
| Vazo-88 | 0.2 |
| Oil Phase 2 | |
| 50/50 Captex 355/ethyl heptanoate | 15.0 |
| ethylidene dimethacrylate | 15.0 |
| TBAEMA | 0.24 |
| CD9055 | 0.24 |
| Water Phase | |
| 5% Selvol 540 PVOH | 45.0 |
| Water | 235.0 |
| V50 | 0.2 |

Oil phase 1 was placed in a steel jacketed reactor, connected to a heating/cooling recirculating water bath. Mixing was done at 650 rpm and the initial temperature was 40° C. The oil was heated to 60° C. and held at 60° C. for 2 hours. Pre-heated oil 2 was added and the combined oils mixed for 30 minutes at 60° C. The pre-heated water phase was added, and mixing started again, at 2000 rpm. Milling at 2000 rpm was continued for 60 minutes. The first 30 minutes of milling were done at 60° C., and during the second 30 minutes of milling, temperature was increased to 75° C. Mixing was at 350 rpm. The batch was heated to 95° C. in 7 hours and held at 95° C. for 6 hours. Table 5 shows the composition of the wall-forming monomer for each.

TABLE 5

Wall-Forming Monomer

| | Ethylidene Dimethacrylate (Acetal Monomer) | Ethylene Glycol Dimethacrylate | Polyethylene Glycol Diacrylate |
|---|---|---|---|
| Comparative Example 6 | 100% | — | — |
| Comparative Example 7 | — | 50% | 50% |
| Example 8 | 50% | — | 50% |
| Comparative Example 9 | — | 66% | 34% |
| Example 10 | 66% | — | 34% |

Table 6 shows the 20% TGA loss for batches made with 50/50 acetal monomer/polyethylene glycol diacrylate, and 50/50 ethylene glycol dimethacrylate/polyethylene glycol diacrylate, compared to a batch made with only acetal monomer as the primary wall-former. The TGA loss temperature data are expressed as a percentage of the initial (1-day) test. Therefore, dropping values in the data represent a lower temperature at which 20% of the core is lost, reflecting the extent of capsule wall degradation.

TABLE 6

20% TGA Loss Temperature Data with 50% polyethylene glycol diacrylate

| Wall Composition | Sample pH | 1 Day | 1 Week | 2 Weeks | 4 Weeks | 8 Weeks |
|---|---|---|---|---|---|---|
| Comparative Example 7: 50/50 ethylene glycol dimethacrylate/ polyethylene glycol diacrylate | 7.0 0.5 | 100.0 100.0 | 102.9 85.5 | 99.1 96.4 | 103.4 89.1 | 97.5 95.1 |
| Example 8: 50/50 acetal monomer polyethylene glycol diacrylate | 7.0 0.5 | 100.0 100.0 | 101.5 107.3 | 97.7 42.6 | 89.9 64.5 | 92.1 29.6 |
| Comparative Example 6: 100% acetal | 0.5 | 100.0 | 137.9 | 98.8 | 89.7 | 87.8 |

The results indicate that with 100% acetal monomer, aged for up to 8 weeks at pH 0.5, very little degradation is evident. The 50/50 ethylene glycol dimethacrylate/polyethylene glycol diacrylate samples show no degradation for up to 8 weeks aging, at either pH 7 or pH 0.5. The samples that consist of 50/50 acetal monomer/polyethylene glycol diacrylate exhibit no degradation at up to 8 weeks of aging at pH 7. However, at pH 0.5 degradation is evident after about 2 weeks.

These results demonstrate the latent degradability of acetal groups incorporated into the capsule wall. Degradation is very limited, even under conditions expected to create hydrolysis (pH 0.5), when only acetal groups are used as the primary wall-former.

Table 7 shows 10% TGA loss results for another similar data series. In this case, a lower level of polyethylene glycol diacrylate is used to modify the wall materials. The batches compared in this series consist of 66/34 ethylene glycol dimethacrylate/polyethylene glycol diacrylate or 66/34 acetal monomer/polyethylene glycol diacrylate, compared to capsules made with acetal monomer as 100% of the primary wall-former. When only 34% of the primary wall former is polyethylene glycol diacrylate (66/34 acetal monomer/polyethylene glycol diacrylate, pH 0.5), degradation does not become evident after 4 weeks. The data suggests that degradability can be "tuned" by the addition of modifying monomers to adjust the capsule wall to be more polar (less hydrophobic).

TABLE 7

10% TGA Loss Temperature Data with 34% polyethylene glycol diacrylate

| Wall Composition | Sample pH | 1 Day | 1 Week | 2 Weeks | 4 Weeks | 8 Weeks |
|---|---|---|---|---|---|---|
| 66/34 ethylene glycol dimethacrylate/ polyethylene glycol diacrylate | 7.0 0.5 | 100.0 100.0 | 97.3 101.0 | 97.3 93.9 | 93.9 91.8 | 90.4 93.7 |
| 66/34 acetal monomer polyethylene glycol diacrylate | 7.0 0.5 | 100.0 100.0 | 97.5 99.6 | 98.7 101.0 | 97.9 61.6 | 97.0 46.3 |
| 100% acetal | 0.5 | 100.0 | 100.0 | 96.5 | 93.4 | 94.9 |

Results from Examples 6-10 suggest that the degradability of acrylate microcapsule wall formed in the presence of oil-phase core is latent. The latent degradability can be realized and refined by modifying the wall structure using added polar monomers.

The microcapsules of the invention are robust but not subject to degradation under acidic pH conditions.

Microcapsules were diluted to about 10% and pH adjusted to either near 7 (neutral) or 0.5 (strongly acidic conditions that would be expected to degrade acetal functionality). Samples were gently agitated and sampled at various time intervals for evaluation by thermogravimetric analysis (TGA). The temperature, at which a specific loss of core was achieved as samples were heated, was determined. It was expected that if capsule wall degradation were to occur, the capsule core would release at a reduced temperature compared to the undegraded microcapsules. The temperature at which 10% or 20% of the core was lost, was determined as reflected.

Example 11

Prepare oil phase one in the reactor with a mill blade, and oil phase two in a beaker with a magnetic stirrer. Prepare water phase in a beaker with a magnetic stirrer. Agitate oil phase in the reactor with a mill blade, blanketed with nitrogen. Heat the reactor from 35 C to 70 C in 45 minutes. Hold at 70 C for 45 minutes, then cool from 75 C to 50 C over 45 minutes. Add oil phase 2 to the reactor, which had been preheated to 50 C for 30 minutes, and let the two oil phases react at 50 C for 10 minutes. Stop the mixing and add the water phase to the reactor, which had been preheated to 50 C for 30 minutes prior to addition. Set the mill speed and start the mixer. Mill for 1 hour. After milling, remove the mill blade and replace with a mixing blade. Heat the batch from 50 C to 75 C in 60 minutes, then hold at 75 C for 240 minutes. Next, ramp from 75 C to 95 C in 60 minutes, then hold at 95 C for 360 minutes. Then cool the batch to room temperature.

Wafer of Wall Material of Examples 12 to 28:

For each of the samples, a 5 g mixture of wall material (i.e. SR206, CD9055, PLA, polar monomer) was added to the compartment of a silicone ice cube tray, and 5 g of the perfume solution (perfume with diluent and initiators) was added as well.

The ice cube tray was placed inside of a custom reactor. Each of the cells was stirred with a clean wooden stick. The "ice cube tray reactor" was covered with aluminum foil (triple-folded layer) and then covered with the reactor cover and the temperature program was begun. The reactor was programmed to heat from 40 C to 60 C in 30 minutes, hold at 60 C for 180 minutes, heat from 60 to 75 C in 30 minutes, heat from 75 to 95 C in 420 minutes, hold at 95 C for 360 minutes, cool from 95 to 55 C in 120 minutes, cool from 55 to 25 C in 360 minutes, and hold at 25 C. This temperature program simulates one process for acrylate capsules using SR206 wall material. This process produces wafers representative of capsule wall material.

The next day, the wafers were removed from their cells. Excess oil was dried off and the starting weight of each wafer was recorded. The wafers were stored between blotting paper until ready for testing. Dimensions of the wafers were 1.75"×1.75"×0.25" (4.45 cm×4.45 c×0.64 cm).

Method for Degradation Measurement

When all the wafers were made, each wafer was placed into a separate, labelled 1-pint (0.47 liter) canning jar. The wafer was covered with deionized water until completely submerged, and the canning lid and ring were placed on the jars. The jars were placed in a 38.1C water bath.

At specific intervals, each wafer was removed from the jar, rinsed off into the jar and placed on a drying rack. The wafer was weighed the following day. The water that was in the jar was vacuum filtered, weighed and the amount of solid material in the water was measured using a CEM solids oven. Also, since there was debris captured on the filter, the filter paper was allowed to dry on a rack. The amount of debris was calculated by weighing the dried filter, brushing the debris back into the jar, and re-weighing the filter.

To calculate the weight loss, the new weight of the wafer, the weight of solid material measured in the filtrate and the weight of the debris are added together to determine the aged wafer weight, which is compared to the starting weight. A percentage of loss is calculated.

Example 12

Wafer was prepared according to the previously described procedure using the following composition: 5 g of perfume solution (perfume with diluent and initiators), 1.5 g of SR206, 1.5 g of CN975, and 2 g of SR415.

Example 13

Wafer was prepared according to the previously described procedure using the following composition: 5 g of perfume solution (perfume with diluent and initiators), 4.875 g of SR206, and 0.125 g of CD9055.

Example 14

Wafer was prepared according to the previously described procedure using the following composition: 5 g of perfume solution (perfume with diluent and initiators), 2.875 g of SR206, 0.125 g of CD9055, and 2 g of SR415.

Example 15

Wafer was prepared according to the previously described procedure using the following composition: 5 g of perfume solution (perfume with diluent and initiators), 1.5 g of SR239, 1.5 g of CN975, and 2 g of SR415.

Example 16

Wafer was prepared according to the previously described procedure using the following composition: 5 g of perfume solution (perfume with diluent and initiators), 4.875 g of SR239, and 0.125 g of CD9055.

Example 17

Wafer was prepared according to the previously described procedure using the following composition: 5 g of perfume solution (perfume with diluent and initiators), 2.875 g of SR239, 0.125 g of CD9055, and 2 g of SR415.

Example 18

Wafer was prepared according to the previously described procedure using the following composition: 5 g of perfume solution (perfume with diluent and initiators), 1.5 g of SR348, 1.5 g of CN975, and 2 g of SR415.

Example 19

Wafer was prepared according to the previously described procedure using the following composition: 5 g of perfume solution (perfume with diluent and initiators), 4.875 g of SR348, and 0.125 g of CD9055.

Example 20

Wafer was prepared according to the previously described procedure using the following composition: 5 g of perfume solution (perfume with diluent and initiators), 2.875 g of SR348, 0.125 g of CD9055, and 2 g of SR415.

Example 21

Wafer was prepared according to the previously described procedure using the following composition: 5 g of perfume solution (perfume with diluent and initiators), 3.625 g of SR206, 0.125 g of CD9055, and 1.25 g of PLA-DM.

Example 22

Wafer was prepared according to the previously described procedure using the following composition: 5 g of perfume solution (perfume with diluent and initiators), 1.625 g of SR206, 0.125 g of CD9055, 2 g of SR415, and 1.25 g of PLA-DM.

Example 23

Wafer was prepared according to the previously described procedure using the following composition: 5 g of perfume solution (perfume with diluent and initiators), 2.4375 g of SR206, 2.4375 g of CN975, and 0.125 g of CD9055.

Example 24

Wafer was prepared according to the previously described procedure using the following composition: 5 g of perfume solution (perfume with diluent and initiators) and 2.5 g of a diluent oil, and 5 g of SR206.

Example 25

Wafer was prepared according to the previously described procedure using the following composition: 5 g of perfume solution (perfume with diluent and initiators), 2.375 g of SR206, 2.375 g of CN975, and 0.25 g of TBAEMA.

Example 26

Wafer was prepared according to the previously described procedure using the following composition: 5 g of perfume solution (perfume with diluent and initiators), 1.5 g of SR206, 1.5 g of CN975, and 2 g of SR415.

Example 27

Wafer prepared according to the previously described procedure using the following composition: 5 g of perfume solution (perfume with diluent and initiators), 2.625 g of SR206, 0.125 g of CD9055, 2 g of SR415, and 0.25 g of TBAEMA.

Example 28

Wafer prepared according to the previously described procedure using the following composition: 5 g of perfume solution (perfume with diluent and initiators), 1.5 g of SR206, 1.25 g of CN975, 0.25 g of CD9055, 2 g of SR415, and 0.25 g of TBAEMA.

Wafer Studies for Degradation

In order to evaluate the impact of various monomer compositions and, in particular, the extent of polar monomers with HPI equal or larger than 20, solid wafers with the monomer compositions (percent by weight) were used, examples 12-28. Table 8 shows the % polar monomer of each of these examples and the resultant 8-week weight loss.

TABLE 8

| Example # | Wafer # | % Polar Monomer (HPI > 20) | 8 Week Wt Loss (%) |
|---|---|---|---|
| 12 | 1 | 40.0 | 33.06 |
| 13 | 2 | 2.5 | 6.02 |
| 14 | 3 | 42.5 | 32.26 |
| 15 | 4 | 40.0 | 32.22 |
| 16 | 5 | 2.5 | 3.59 |
| 17 | 6 | 42.5 | 0.98 |
| 18 | 7 | 40.0 | 31.17 |
| 19 | 8 | 2.5 | 4.69 |
| 20 | 9 | 42.5 | 23.91 |
| 21 | 10 | 27.5 | 6.13 |
| 22 | 11 | 67.5 | 33.30 |
| 23 | P16 | 2.5 | 7.86 |
| 24 | P11 | 0 | 6.71 |
| 25 | P10 | 5.0 | 6.69 |
| 26 | P9 | 40.0 | 29.14 |
| 27 | P20 | 47.5 | 31.24 |
| 28 | P3 | 50.0 | 32.85 |

Figure 3:
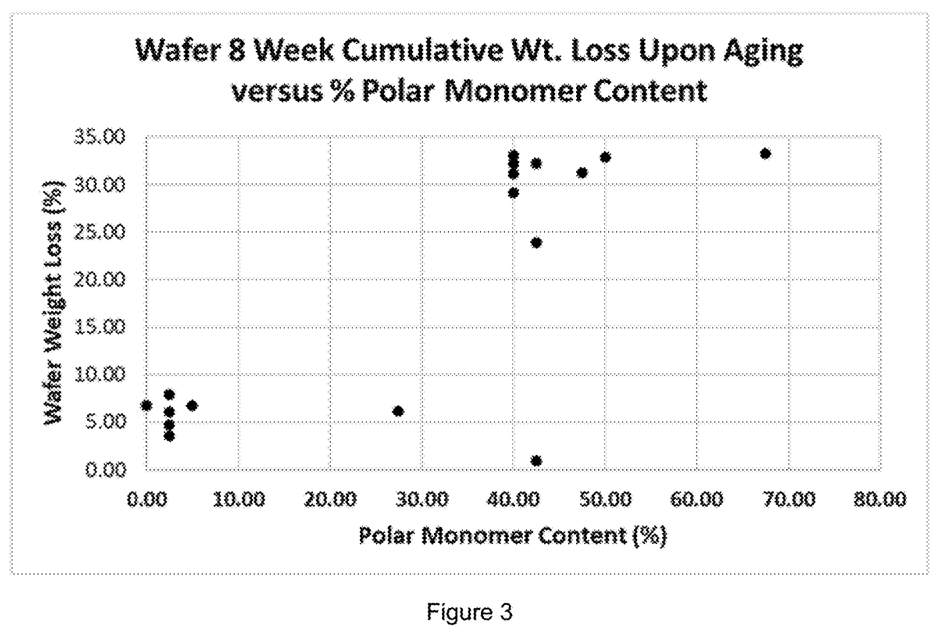
FIG. 3 depicts wafer weight loss upon aging correlated to the percent of polar monomer (hydrophilicity index (HPI) equal of larger than 20).

When the 8-week cumulative weight loss is plotted against the % polar monomer in the monomer mix, it is clear that the more polar monomer there is in the monomer mix, the more degradable the wafer is. See FIG. 3. A polar monomer is monomer with a hydrophilicity index equal to or greater than 20.

Wash and Sensory Evaluations

For some of the wafer compositions, equivalent capsule batches were created according to the process of Example 11, but using the monomer composition of the examples listed in Table 8. The capsules were studied for their leakage and sensory performance when added to scent free fabric conditioner, also known as fabric enhancer.

Capsule slurries were formulated into the fabric conditioner at a fragrance equivalent of 0.5% by weight. Formulations equilibrated overnight (~12 hours). The formulated products were dosed in the rinse cycle at 90 grams. The wash cycle was performed using a scent free laundry detergent.

Figure 4:
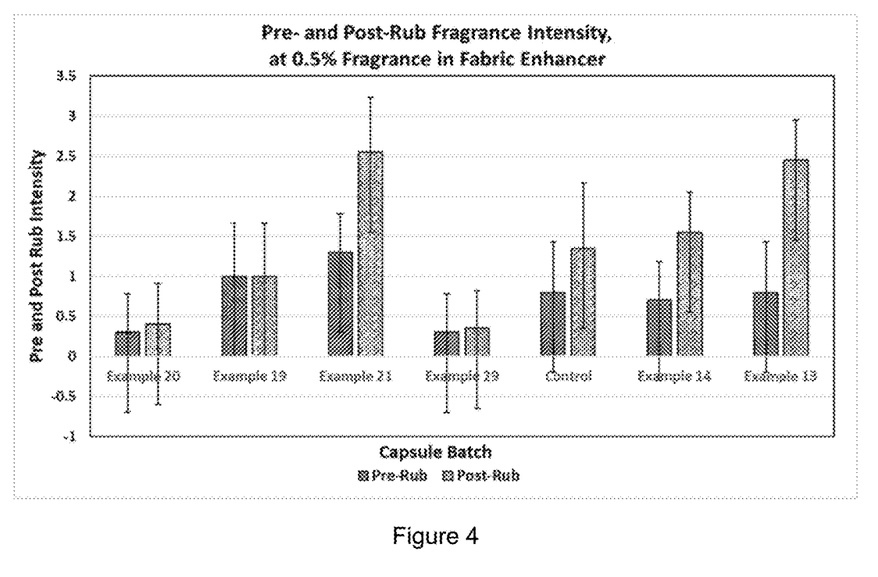
FIG. 4 is a graph of pre- and post-rub fragrance intensity at 0.5% fragrance in fabric enhancer.

The 9 lb. wash load contained a mix of cotton and polyester/cotton blend articles (terry washcloths, T-shirts, pillowcases, and hand towels). Results are shown in Table 9 and in graph form in FIG. 4. Sensory intensities are rated on the following scale: 0=No Odor, 1=Faint Odor, 2=Distinct Odor, 3=Very Strong Odor. Example 29 is unencapsulated fragrance oil.

TABLE 9

| Example | Corresponding wafer | Pre-Rub | Post-Rub | Difference of Post- minus Pre-Rub |
|---|---|---|---|---|
| 20 | 9 | 0.3 | 0.4 | 0.1 |
| 19 | 8 | 1 | 1 | 0 |

TABLE 9-continued

| Example | Corresponding wafer | Pre-Rub | Post-Rub | Difference of Post-minus Pre-Rub |
|---|---|---|---|---|
| 21 | 10 | 1.3 | 2.55 | 1.25 |
| 29 | Unencapsulated fragrance oil | 0.3 | 0.35 | 0.05 |
|  | Control | 0.8 | 1.35 | 0.55 |
| 14 | 3 | 0.7 | 1.55 | 0.85 |
| 13 | 2 | 0.8 | 2.45 | 1.65 |

Figure 5:
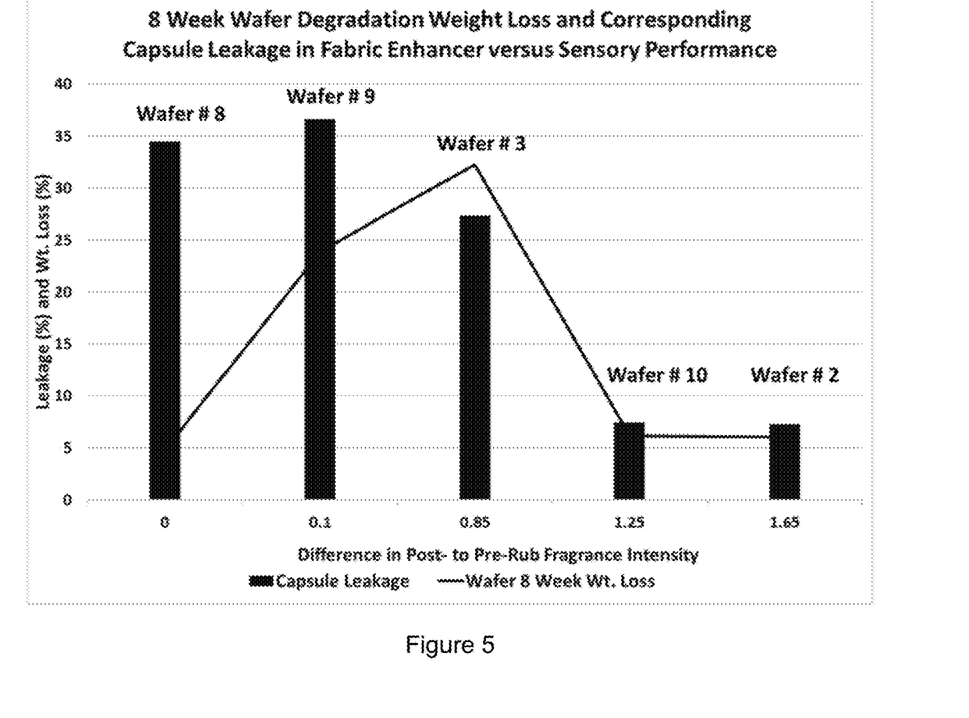
FIG. 5 is a graph of weight loss and leakage versus the difference in post- to pre-rub fragrance intensity.

A comparison was made between the difference in post- to pre-rub sensory intensity versus microcapsule leakage in fabric conditioner and the 8 week weight loss of the degradability measurement. A graphical presentation is shown FIG. 5.

Figure 6:
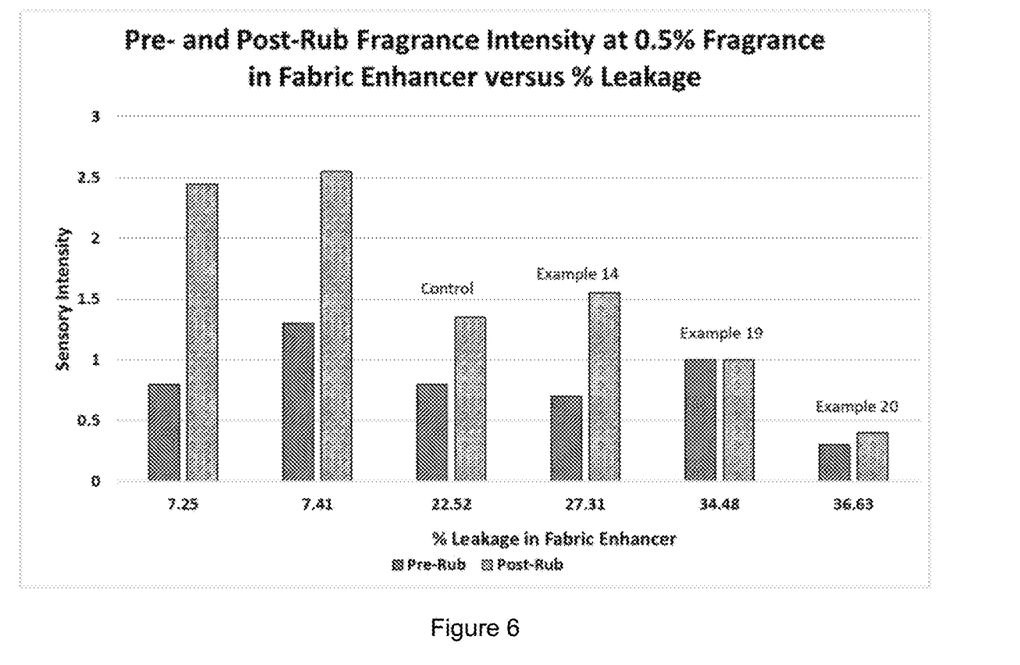
FIG. 6 is a graph of pre- and post-rub fragrance intensity in fabric enhancer.

FIG. 6 shows that sensory performance decreases with increasing microcapsule leakage in fabric enhancer.

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and charges can be made by those skilled in the art without departing from the spirit and scope of the invention.

What we claim is:

1. A population of microcapsules wherein each microcapsule comprises a capsule core and a capsule shell, the capsule shell being hydrolysable characterized by the capsule shell containing polar hydrophilic and acid groups, the population of microcapsules made by an oil-in-water microencapsulation process comprising:
    a) dispersing a polymeric emulsifier and optionally an initiator in water to form a water phase;
    b) dispersing in one or more oil phases to form a composition comprising components i) to v):
        i). an initiator, and a core material,
        ii). a first multifunctional (meth)acrylate monomer having greater than one ester group on average in the monomer and having a hydrophilicity index of less than 20,
        iii). a second multifunctional (meth)acrylate monomer, the second multifunctional (meth)acrylate comprising a hydrophilic multifunctional polar monomer having a hydrophilicity index of at least 30 and said second multifunctional polar monomer comprising 50% or less of the capsule shell, wherein the first and second multifunctional (meth)acrylate monomers together comprise greater than 80% by weight of the capsule shell,
        iv). an acidic (meth)acrylate monomer or at least one oil soluble or dispersible acid or both, the acidic (meth)acrylate monomer having one or more groups which are selected from carboxy and sulfonic groups, and
        v). optionally from 0 to 50% by weight of the capsule shell of an aliphatic polyester, the aliphatic polyester having two or more of acrylate or methacrylate groups;
    c) emulsifying the composition comprising components i) to v) into the water phase under high shear agitation to form an oil-in-water emulsion comprising droplets of the core material and oil phase monomers dispersed in the water phase; and
    d) activating the initiator or initiators by heat or actinic radiation to react the monomers and optional aliphatic polyester thereby forming a capsule shell which is polymeric, surrounding the droplets of the core material; and wherein
    e) the microcapsules of the population of microcapsules have, when measured under controlled composting conditions over 30 days using enumeration analysis average rate of observed numeric loss in a hemocytometer counting chamber of at least 1% per day;
    wherein the capsule shell comprises a reaction product of an additional monomer having a functional group selected from a disulfide, an acetal, a hemiaminal, a thioacetal, a thioketal, a formate, a phosphoester, a phosphase, an anhydride or an orthoester monomer, said additional monomer based on total shell weight constituting from 0.1 to 50 wt % of the capsule shell.

2. The population of microcapsules according to claim 1 wherein the multifunctional (meth)acrylate monomer having greater than one ester group on average in the monomer has an average number of ester groups of at least 1.5.

3. The population of microcapsules according to claim 1 wherein the first multifunctional (meth)acrylate monomer having greater than one ester group on average in the monomer is selected from ethylene glycol dimethacrylate, ethylidene dimethacrylate, trimethylolpropane triacrylate, trimethylolpropane trimethacrylate, pentaerythritol tetraacrylate, tricyclodecane dimethanol dimethacrylate, 1,10 decanediol dimethacrylate, 1,6 hexanediol dimethacrylate, 1,9 nonanediol dimethacrylate, neopentyl glycol dimethacrylate, di-trimethylolpropane tetraacrylate, dipentaerythritol pentaacrylate, ethoxylated (2) bisphenol A dimethacrylate, ethoxylated (3) bisphenol A diacrylate, dipropylene glycol diacrylate, ethoxylated (4) bisphenol A diacrylate, ethoxylated (4) bisphenol A dimethacrylate, and pentaerythritol triacrylate.

4. The population of microcapsules according to claim 1 wherein the hydrophilic multifunctional polar monomer is selected from polyethylene glycol (200) dimethacrylate, ethoxylated (9) trimethylolpropane triacrylate, triacrylate, ethoxylated (30) bisphenol A diacrylate, ethoxylated (15) trimethylolpropane triacrylate, ethoxylated glycerine triacrylate, ethoxylated (20) trimethylolpropane triacrylate, polyethylene glycol (400) dimethacrylate, polyethylene glycol (600) dimethacrylate, ethoxylated pentaerythritol tetraacrylate, polyethylene glycol (1000) dimethacrylate, polyethylene glycol (200) diacrylate, polyethylene glycol (400) diacrylate, polyethylene glycol (600) diacrylate and tris (2-hydroxy ethyl) isocyanurate triacrylate.

5. The population of microcapsules according to claim 1 wherein said second multifunctional methacrylate monomer is selected from the group consisting of diethylene glycol dimethacrylate, ethoxylated (3) trimethylolpropane triacrylate, polypropylene glycol (400) dimethacrylate, ethoxylated (10) bisphenol A dimethacrylate, ethoxylated (10) bisphenol A diacrylate, ethoxylated (4) pentaerythritol tetraacrylate, triethylene glycol dimethacrylate, 2-hydroxyl 1-3 dimethacryloxy propane, ethoxylated (6) trimethylolpropane triacrylate, ethoxylated propyleneglycol dimethacrylate.

6. The population of microcapsules according to claim 1 wherein the acidic (meth)acrylate monomer is selected from carboxyalkyl acrylate or carboxyalkyl methacrylate.

7. The population of microcapsules according to claim 1 wherein the core material is a benefit agent.

8. The population of microcapsules according to claim 7 wherein the benefit agent is selected from one or more of the groups consisting of a fragrance, a perfume, a malodor reducing agent, a pharmaceutical, a nutrient, a fertilizer, a biological active, an essential oil, an herbicide, a lubricant, a dye, an emollient, a phase change material, and a UV absorber.

9. The population of microcapsules according to claim 8 wherein the core material includes in addition a partition modifier.

10. The population of microcapsules according to claim 1 including in addition a deposition aid coated over the capsule shell.

11. The population of microcapsules according to claim 1 wherein mirocapsules of the population of microcapsules have a particle size of from 0.5 to 150 microns.

12. A population of microcapsules wherein each microcapsule comprises a capsule core and a capsule shell, the capsule shell being hydrolysable characterized by the capsule shell containing polar hydrophilic and acid groups, the population of microcapsules made by an oil-in-water microencapsulation process comprising:
  e) dispersing a polymeric emulsifier and optionally an initiator in water to form a water phase;
  f) dispersing in one or more oil phases to form a composition comprising components i) to v);
    i). an initiator, and a core material,
    ii). a first multifunctional (meth)acrylate monomer having greater than one ester group on average in the monomer and having a hydrophilicity index of less than 20,
    iv). an acidic (meth)acrylate monomer or at least one oil soluble or dispersible acid or both, the acidic (meth)acrylate monomer having one or more groups which are selected from carboxy and sulfonic groups,
    v). optionally from 0 to 50% by weight of the capsule shell of an aliphatic polyester, the aliphatic polyester having two or more of acrylate or methacrylate groups;
  g) emulsifying the composition comprising components i) to v) into the water phase under high shear agitation to form an oil-in-water emulsion comprising droplets of core material and oil phase monomers dispersed in the water phase; and
  h) activating the initiator or initiators by heat or actinic radiation to react the monomers and optional alipathic polyester thereby forming a capsule shell which is polymeric, surrounding the droplets of the core material; and wherein
  e) the microcapsules of the population of microcapsules have, when measured under controlled composting conditioned over 30 days using enumeration analysis an average rate of observed numeric loss in a hemocytometer counting chamber of at least 1% per day; and
wherein the aliphatic polyester comprises an oligomer, polymer or copolymer of one or more of lactic acid, caprolactone, or glycolic acid.

13. The population of microcapsules according to claim 1 wherein microcapsules of the population of microcapsules are cationic.

14. An article of manufacture incorporating the population of microcapsules according to claim 1.

15. The article of manufacture according to claim 14, wherein the article is selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and insulation.

* * * * *